US010650913B2

(12) United States Patent
Sato (10) Patent No.: US 10,650,913 B2
(45) Date of Patent: May 12, 2020

(54) INTERACTION ENERGY CALCULATION METHOD, CALCULATION DEVICE, AND PROGRAM

(71) Applicant: FUJITSU LIMITED, Kawasaki-shi, Kanagawa (JP)

(72) Inventor: Hiroyuki Sato, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 324 days.

(21) Appl. No.: 15/616,424

(22) Filed: Jun. 7, 2017

(65) Prior Publication Data

US 2017/0270281 A1 Sep. 21, 2017

Related U.S. Application Data

(63) Continuation of application No. PCT/JP2014/084022, filed on Dec. 24, 2014.

(51) Int. Cl.
*G06F 17/50* (2006.01)
*G16C 10/00* (2019.01)
(Continued)

(52) U.S. Cl.
CPC ............ *G16C 10/00* (2019.02); *G06F 30/20* (2020.01); *G16B 5/00* (2019.02); *G16B 15/00* (2019.02)

(58) Field of Classification Search
USPC .......... 703/2, 7, 9, 11; 702/19, 172; 514/301
See application file for complete search history.

(56) References Cited

U.S. PATENT DOCUMENTS 7,467,046 B2 * 12/2008 Taylor .................. C12N 9/1085
702/19
7,756,674 B2 * 7/2010 Young .................... G16C 20/30
702/172

(Continued)

FOREIGN PATENT DOCUMENTS

JP 2006-508421 3/2006
JP 2006-209764 8/2006
(Continued)

OTHER PUBLICATIONS

International Search Report dated Apr. 7, 2015 in corresponding International Application No. PCT/JP2014/084022.
(Continued)

*Primary Examiner* — Thai Q Phan
(74) *Attorney, Agent, or Firm* — Staas & Halsey LLP (57) ABSTRACT

A method, which includes: extracting one or more calculation-target water molecules that influence at least interaction energy between the target molecule and some of the drug candidate molecules, but not the interaction energy between the target molecule and all of the drug candidate molecules; and calculating each interaction energy between the target molecule and each of the drug candidate molecules with only considering the one or more calculation-target water molecules as water molecules treated positively in a calculation of each interaction energy, and with considering the one or more calculation-target water molecules only in a calculation of interaction energy which the one or more calculation-target water molecules influence, wherein the method is a method for calculating interaction energy between the target molecule and the drug candidate molecules using a calculator.

9 Claims, 8 Drawing Sheets

(51) Int. Cl.
  *G16B 15/00* (2019.01)
  *G16B 5/00* (2019.01)
  *G06F 30/20* (2020.01)

(56) References Cited

U.S. PATENT DOCUMENTS

| | | | | |
|---|---|---|---|---|
| 8,785,499 | B2* | 7/2014 | Mackerell, Jr. | C07C 251/86 514/614 |
| 2004/0010525 | A1 | 1/2004 | Bennett et al. | |
| 2010/0241412 | A1* | 9/2010 | Young | G16C 20/30 703/11 |
| 2012/0190708 | A1* | 7/2012 | Mackerell, Jr. | C07C 251/86 514/301 |
| 2014/0358450 | A1* | 12/2014 | Barril Alonso | G16B 15/00 702/19 |

FOREIGN PATENT DOCUMENTS

| | | |
|---|---|---|
| JP | 2010-117986 | 5/2010 |
| JP | 2014-215785 | 11/2014 |
| WO | WO 2005/029351 A1 | 3/2005 |

OTHER PUBLICATIONS

Written Opinion of the International Searching Authority, PCT/ISA/237, dated Apr. 7, 2015 in corresponding International Application No. PCT/JP2014/084022.

Ozawa et al., "Application of fragment molecular orbital (FMO) method for molecular simulation in drug discovery", [online],2009,[retrieval date Mar. 20, 2015(Mar. 20, 2015)],Internet URL:https://www.jamstec.go.jp/es/jp/info/sangyou21_pdf/p07-2.pdf.

Misoo et al., "Development of Molecular Dynamics Programs for Proteins with a Parallelized Barnes-Hut Tree Code", Joint Symposium on Parallel Processing 1999, Jun. 9, 1999 (Jun. 9, 1999), vol. 99, No. 6, pp. 143 to 150.

Kitaura et al., "Fragment molecular orbital method: an approximate computational method for large molecules", Chemical Physics Letters, 313,(1999), Nov. 12, 1999, pp. 701-706.

Fedorov et al., "The Polarizable Continuum Model (PCM) Interfaced with the Fragment Molecular Orbital Method (FMO)", Journal of Computational Chemistry 27, pp. 976-985 (2006).

Extended European Search Report dated Dec. 1, 2017 in corresponding European Patent Application No. 14908944.3.

Hardik I. Parikh et al.: "Intuitive, but not simple: Including explicit water molecules in protein—protein docking simulations improves model quality," Proteins: Structure, Function, and Bioinformatics, vol. 82, No. 6, Dec. 9, 2013, pp. 916-932.

Panagiotis L. Kastritis et al.: "Solvated protein—protein docking using Kyte—Doolittle-based water preferences," Proteins: Structure, Function, and Bioinformatics, vol. 81, No. 3, Dec. 24, 2012, pp. 510-518.

Communication pursuant to Article 94(3) EPC, dated Nov. 6, 2019, in European Application No. 14908944.3 (9 pp.).

* cited by examiner

INTERACTION ENERGY CALCULATION METHOD, CALCULATION DEVICE, AND PROGRAM

CROSS-REFERENCE TO RELATED APPLICATION

This application is a continuation application of International Application PCT/JP2014/084022 filed on Dec. 24, 2014 and designated the U.S., the entire contents of which are incorporated herein by reference.

FIELD

The embodiments discussed herein relate to a method for calculating interaction energy between a target molecule and drug candidate molecules, a calculation device, and a program for causing a computer to execute the calculation method.

BACKGROUND

When certain protein has a functional site that adversely affects human bodies, it is important to design a ligand that stably bonds with the functional site of the protein in drug discovery for the protein serving as a target. The functional site of the protein is blocked by stabling bonding the ligand to the protein. As a result, the adverse effect of the protein to human bodies can be prevented.

In order to judge whether a bond between the protein and the ligand is stable or not, typically, a technique for highly accurately determining interaction energy between the protein and the ligand using a method based on quantum mechanics (QM) has been commonly used (see, for example, Kazuo Kitaura, Eiji Ikeo, Toshio Asada, Tatsuya Nakano, Masami Uebayasi, Chemical Physics Letters, 313, (1999), 701-706).

The method based on QM has a problem that a calculation time exponentially increases, as the number of atoms of a calculation target increases. The number of atoms for only a complex of the protein and the ligand may be a few thousands, but the number of atoms may be a several tens thousands when water molecules present around the complex are included. Accordingly, there is a problem in a calculation time when a QM calculation including water molecules is performed.

In order to achieve efficiency of the interaction energy calculation, a technique for approximating water molecules with a solvent as a uniform continuum has been proposed (see, for example, D. G. Fedorov, K. Kitaura, H. Li, J. H. Jensen, M. S. Gordon, J. Comput. Chem. 27, 976-985 (2006)). In the proposed technique, the number of atoms does not increase, and therefore an exponential increase of the calculation time can be avoided.

In the proposed technique, however, the continuum approximation is destroyed when a complex of the protein and the ligand is bonded to water with hydrogen bonds. In order to determine appropriate interaction energy, therefore, water is expressly considered, which is not efficient in terms of a calculation time.

There is a case where a drug candidate molecule having large interaction energy with a target molecule, such as protein, is estimated among a plurality of drug candidate molecules (ligand). In this case, each interaction energy between the target molecule and each of the drug candidate molecules is determined in the presence of water molecules. Then, the obtained values of the interaction energy are compared. When the values of the interaction energy are compared, reliability of a relative relationship between the values of the obtained interaction energy is more important than absolute values of the interaction energy. Therefore, there is a need for efficiently calculating interaction energy having a relative relationship of high reliability. However, the above-described proposed techniques do not sufficiently meet such a need.

SUMMARY

The disclosed method for calculating interaction energy between a target molecule and drug candidate molecules, the method includes: extracting one or more calculation-target water molecules that influence at least interaction energy between the target molecule and some of the drug candidate molecules, but not the interaction energy between the target molecule and all of the drug candidate molecules; and calculating each interaction energy between the target molecule and each of the drug candidate molecules with only considering the one or more calculation-target water molecules as water molecules treated positively in a calculation of each interaction energy, and with considering the one or more calculation-target water molecules only in a calculation of interaction energy which the one or more calculation-target water molecules influence, wherein the method is a method for calculating interaction energy between the target molecule and the drug candidate molecules using a calculator.

The disclosed program for causing a computer to execute a method including:

extracting one or more calculation-target water molecules that influence at least interaction energy between a target molecule and some of drug candidate molecules, but not the interaction energy between the target molecule and all of the drug candidate molecules; and calculating each interaction energy between the target molecule and each of the drug candidate molecules with only considering the one or more calculation-target water molecules as water molecules treated positively in a calculation of each interaction energy, and with considering the one or more calculation-target water molecules only in a calculation of interaction energy which the one or more calculation-target water molecules influence.

The disclosed calculation device includes:

an extracting unit configured to extract one or more calculation-target water molecules that influence at least interaction energy between a target molecule and some of drug candidate molecules, but not the interaction energy between the target molecule and all of the drug candidate molecules; and a calculating unit configured to calculate each interaction energy between the target molecule and each of the drug candidate molecules with only considering the one or more calculation-target water molecules as water molecules treated positively in a calculation of each interaction energy, and with considering the one or more calculation-target water molecules only in a calculation of interaction energy which the one or more calculation-target water molecules influence.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Method for Calculating Interaction Energy

The disclosed method for calculating interaction energy is a method for calculating a target molecule and drug candidate molecules using a calculator.

The method for calculating interaction energy includes a calculation-target water molecule extraction step and an interaction energy calculation step, and may further include other step according to the necessity.

The method for calculating interaction energy is performed by using a calculator. The number of the calculators used for the method for calculating interaction energy may be one, or two or more. For example, a plurality of the calculator may be allowed to execute the method for calculating interaction energy with decentralizing.

The disclosed embodiments aim to solve the above-described various problems existing in the art, and to achieve the following object. Specifically, the present disclosure has an object to provide a method for calculating interaction energy, which can efficiently calculate interaction energy having a highly-reliable relative relationship, a calculation device, and a program for executing the calculation method.

The disclosed method for calculating interaction energy can solve the above-described various problems existing in the art, can achieve the above-described object, and can efficiently calculate interaction energy having a highly-reliable relative relationship.

The disclosed program can solve the above-described various problems existing in the art, can achieve the above-described object, and can efficiently calculate interaction energy having a highly-reliable relative relationship.

The disclosed calculation device can solve the above-described various problems existing in the art, can achieve the above-described object, and can efficiently calculate interaction energy having a highly-reliable relative relationship.

Figure 1:
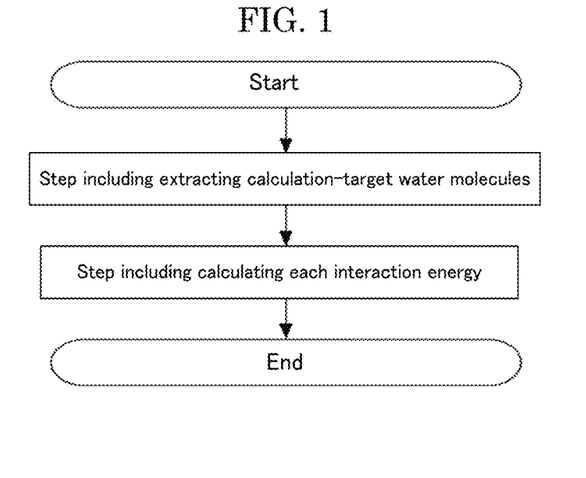
FIG. 1 is a flowchart for explaining the disclosed method for calculating interaction energy.

FIG. 1 is a flowchart for explaining the method for calculating interaction energy.

First a calculation-target water molecule extraction step is performed. In this step, extracted are one or more calculation-target water molecules that influence at least interaction energy between the target molecule and some of the drug candidate molecules, but not the interaction energy between the target molecule and all of the drug candidate molecules.

Next, an interaction energy calculation step is performed. In this step, each interaction energy between the target molecule and each of the drug candidate molecules is calculated with only considering the one or more calculation-target water molecules as water molecules treated positively in a calculation of each interaction energy, and with considering the one or more calculation-target water molecules only in a calculation of interaction energy which the one or more calculation-target water molecules influence.

In a calculation of interaction energy between a target molecule and a drug candidate molecule, a calculation becomes complex and the calculation cannot be performed efficiently, if water molecules surrounding a complex formed of the target molecule and the drug candidate molecule are treated positively, and all of the water molecules are considered.

On the other hand, an accuracy of a calculation significantly decreases, if water molecules are not considered in the calculation of the interaction energy.

In the disclosed method for calculating interaction energy, one or more water molecules that influence at least interaction energy between the target molecule and some of the drug candidate molecules, but not the interaction energy between the target molecule and all of the drug candidate molecules are extracted, and only the extracted water molecules are considered as water molecules treated positively in the calculation of the interaction energy. Whether such water molecules are considered in the calculations of interaction energy or not influences a relative relationship between calculated values of the interaction energy. The calculated values of the interaction energy can be prevented from being complex by considering only such water molecules as water molecules treated positively in the calculations of interaction energy, in other words, not considering water molecules other than the above-described water molecules as water molecules treated positively in the calculations of the interaction energy. Moreover, reliability of a relative relationship in calculated values of interaction energy can be enhanced by considering the above-described water molecules as water molecules treated positively in the calculations of the interaction energy.

Calculation-Target Water Molecule Extraction Step

In the calculation-target water molecule extraction step, one or more water molecules that influence that influence at least interaction energy between the target molecule and some of the drug candidate molecules, but not the interaction energy between the target molecule and all of the drug candidate molecules are extracted. In the present specification and claims, the one or more water molecules extracted in the step are referred to as one or more calculation-target water molecules.

The number of calculation-target water molecules extracted in the calculation-target water molecule extraction step may be one, or two or more.

The target molecule is not particularly limited and may be appropriately selected depending on the intended purpose. Examples of the target molecule include protein, ribonucleic acid (RNA), and deoxyribonucleic acid (DNA).

In the present specification, the water molecules that influence interaction energy means water molecules which change a value of interaction energy between when the water molecules are considered in a calculation of the interaction energy and when the water molecules are not considered in the calculation of the interaction energy.

The calculation-target water molecule extraction step preferably includes a below-described first treatment, a below-described second treatment, and a below-described non-overlapping water molecule extraction treatment because reliability of a relative relationship between calculated values of interaction energy is enhanced.

Note that, the first treatment and the second treatment are treatments performed in one interaction-calculation-target space including the target molecule and one drug candidate molecule among the drug candidate molecules.

The non-overlapping water molecule extraction treatment is a treatment performed by comparing at least interaction-calculation-target spaces each including the calculation-target water molecules among all of the interaction-calculation-target spaces each including the target molecule and the drug candidate molecules.

In the present specification, the interaction-calculation-target space means a space including the target molecule and one drug candidate molecule when one interaction energy is calculated.

First Treatment

In the first treatment, one or more water molecules that interact with both the target molecule and the one drug candidate molecule are extracted. In the present specification and claims, the one or more water molecules extracted in the first treatment are referred to as one or more interaction water molecules.

In the present specification, the interaction means non-bonding interaction. Examples of the non-bonding interaction include electrostatic interaction and Van der Waals interaction.

Typically, a plurality of the interaction water molecules, which are extracted in the first treatment, are present in the interaction-calculation-target space.

Examples of a method for extracting the one or more interaction water molecules in the first treatment include a method where one or more water molecules distances from which to both the target molecule and the one drug candidate molecule are a threshold or less are extracted as the one or more interaction water molecules.

For the threshold, a value set as a default value in a calculator in advance may be used, or a value appropriately set by a user may be used.

Examples of the threshold include 6 angstroms. Specifically, examples of the method for extracting the one or more interaction water molecules include a method where one or more water molecules distances from which to both the target molecule and the one drug candidate molecule are 6 angstroms or less are extracted as the one or more interaction water molecules.

For example, a distance between the target molecule and the water molecule is a distance between a surface of the target molecule and an oxygen atom of the water molecule.

For example, a distance between the drug candidate molecule and the water molecule is a distance between a surface of the drug candidate molecule and an oxygen atom of the water molecule.

Second Treatment

In the second treatment, one or more water molecules are extracted from the one or more interaction water molecules extracted in the first treatment based on a fluctuation width of coordinates of each of the one or more interaction water molecules, or occurrence frequency of each of the one or more interaction water molecules, or both. In the present specification and claims, the one or more water molecules extracted in the second treatment are referred to as one or more calculation-candidate water molecules.

In the second treatment, the one or more calculation-candidate water molecules are preferably extracted from the one or more interaction water molecules extracted in the first treatment based on a fluctuation width of coordinates of each of the one or more water molecules and occurrence frequency of each of the one or more water molecules, because reliability of a relative relationship between calculated values of interaction energy is enhanced.

The fluctuation width of the coordinates of each of the one or more calculation-candidate water molecules and the occurrence frequency of each of the one or more calculation-candidate water molecules are preferably determined by molecular dynamic simulation.

For example, the function width of coordinates of the calculation-candidate water molecules can be determined by performing molecular dynamic simulation on the target molecule, the one drug candidate molecule, and the interaction water molecule, analyzing coordinates of each of the interaction water molecules, and evaluating with root mean square fluctuation (RMSF). The formula for determining the RMSF is presented below.

$$RMSF(W) = \sqrt{\frac{1}{T}\sum_{t=1}^{T}(W(t) - W_{REF})^2}$$

In the formula above, W(t) is coordinates of an interaction water molecule at time t, $W_{REF}$ is coordinates of a reference interaction water molecule, and T is a simulation time.

The interaction water molecule having a small value of the RMSF(W) stays on coordinates which is in a short distance from both a target molecule and one drug candidate molecule, and therefore the interaction water molecule has a large influence on interaction between the target molecule and the one drug candidate molecule.

When the one or more calculation-candidate water molecules are extracted based on the fluctuation width of coordinates of each of the calculation-candidate water molecules, extraction may be performed with setting a threshold. Examples of a method for extracting one or more calculation-target water molecules based on a fluctuation width of coordinates of each of the calculation-target water molecules include a method where interaction one or more water molecules whose RMSF is 2 angstroms or less are extracted. For the threshold, a value set as a default value in a calculator in advance may be used, or a value appropriately set by a user may be used.

For example, the occurrence frequency of the interaction water molecules can be determined by performing molecular dynamic simulation on the target molecule, the one drug candidate molecule, and the interaction water molecules, determining a density distribution of the interaction water molecules obtained by placing all of the interaction water molecules over a total time duration of the molecular dynamic simulation in one space, and determining the occurrence frequency from the density distribution. Interaction water molecules are frequently present on coordinates having high occurrence frequency of the interaction water molecules, even though the interaction water molecules are not particular water molecules. Accordingly, it can be assumed that virtual water molecules are constantly present on coordinates having high occurrence frequency of interaction water molecules. The virtual water molecules present on coordinates having high occurrence frequency of interaction water molecules stay on coordinates which are in a short distance from both the target molecule and the one drug candidate molecule, similar to the case of the interaction water molecules having a small fluctuation width of coordinates. Therefore, such virtual water molecules has a large influence on interaction between the target molecule and the one drug candidate molecule.

As described above, interaction water molecules extracted based on the occurrence frequency of each of the interaction water molecules are not particular water molecules, but virtual water molecules.

Examples of a method for selecting coordinates having high occurrence frequency of interaction water molecules include a method where coordinates of the higher density (e.g., a density of 10 times or more) than a density of a predetermined low density region in a density distribution of interaction water molecules are selected.

The molecular dynamic simulation can be performed using a molecular dynamic calculation program. Examples of the molecular dynamic calculation program include AMBER, CHARMm, GROMACS, GROMOS, NAMD, and myPresto.

Non-Overlapping Water Molecule Extraction Treatment

In the non-overlapping water molecule extraction treatment, at least interaction-calculation-target spaces each including the calculation-candidate water molecules among all of the interaction-calculation-target spaces each including the target molecule and the drug candidate molecules are compared to extract one or more water molecules, which do not have identical coordinates in all of the interaction-calculation-target spaces, from the calculation-candidate water molecules.

The non-overlapping water molecule extraction treatment may be a treatment where at least interaction-calculation-target spaces each including the calculation-candidate water molecules among all of the interaction-calculation-target spaces each including the target molecule and the drug candidate molecules are compared to exclude one or more water molecules, which have identical coordinates in all of the interaction-calculation-target spaces, among the calculation-candidate water molecules.

Note that, water molecules on the same coordinates in all of the complexes each including the target molecule and the drug candidate molecule among the calculation-candidate water molecules extracted in the second treatment may influence interaction energy between the target molecule and the drug candidate molecule itself, but do not influence a relative relationship of all of the values of the interaction energy. Accordingly, to consider such water molecules in a calculation of interaction energy merely leads to high complexity of calculation.

The first treatment, the second treatment, and the non-overlapping water molecule extraction treatment, which are one example of the calculation-target water molecule extraction step, are explained with reference to FIGS. 2, 3, 4, 5, 6A, and 6B.

Figure 2:
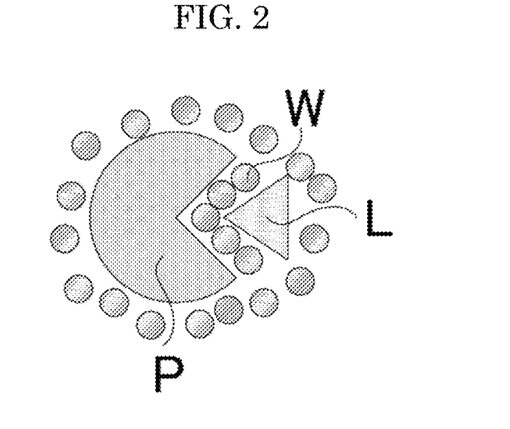
FIG. 2 is a schematic view illustrating a complex of a target molecule P and a drug candidate molecule L, and water molecules W surrounding the complex.

FIG. 2 is a schematic view illustrating a complex of a target molecule P and a drug candidate molecule L, and water molecules W surrounding the complex. The complex is present in one interaction-calculation-target space. The large number of water molecules W are present in the surrounding area of the complex.

Figure 3:
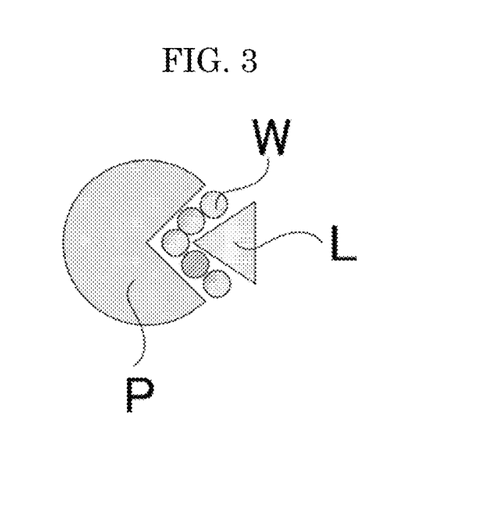
FIG. 3 is a schematic view for explaining a first treatment.

First, water molecules W that interact with both the target molecule P and the drug candidate molecule L are selected among the large number of the water molecules W in the first treatment, as illustrated in FIG. 3. Typically, water molecules W to be extracted are water molecules W which are in a short distance from both the target molecule P and the drug candidate molecule L.

Figure 4:
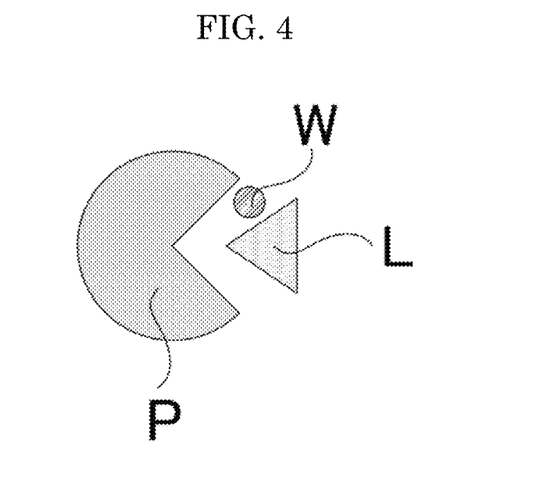
FIG. 4 is a schematic view for explaining a second treatment.
Figure 5:
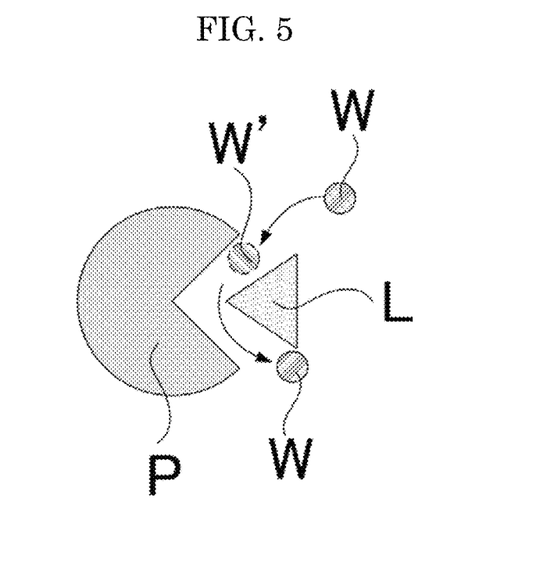
FIG. 5 is a schematic view for explaining a second treatment.

Next, water molecules are further extracted from the water molecules W extracted in the first treatment, based on fluctuation width of coordinates of each of the water molecules W (FIG. 4), or occurrence frequency of each of the water molecules W (FIG. 5), or both, in the second treatment, as illustrated in FIGS. 4 and 5. The water molecule extracted based on occurrence frequency of a water molecule W is a virtual water molecule W'. On the coordinates of the virtual water molecule W', a water molecule W is frequently present.

Figure 6A:
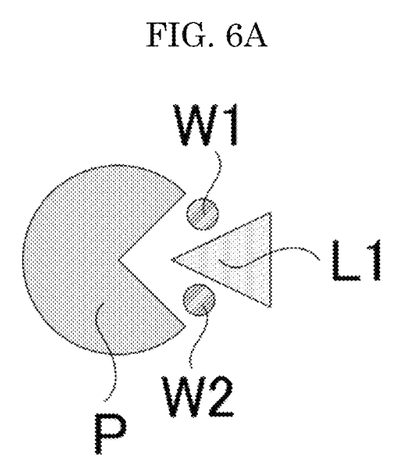
FIG. 6A is a schematic view for explaining a non-overlapping water molecule extraction treatment.
Figure 6B:
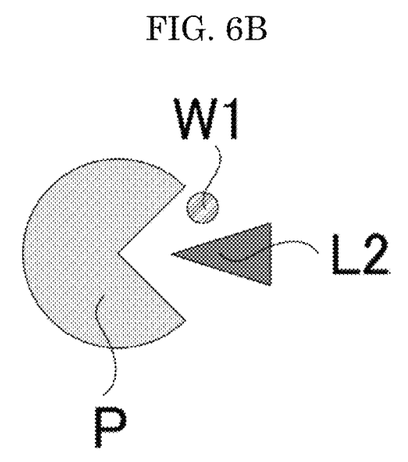
FIG. 6B is a schematic view for explaining a non-overlapping water molecule extraction treatment.

Next, in the non-overlapping water molecule extraction treatment, at least interaction-calculation-target spaces each including the calculation-candidate water molecules are compared among all of the interaction-calculation-target spaces, and water molecules W which are not on the same coordinates in all of the interaction-calculation-target spaces are extracted from the water molecules extracted in the second treatment. One example of the non-overlapping water molecule extraction treatment of a case where two drug candidate molecules are used in the disclosed method for calculating interaction energy is explained below. As illustrated in FIG. 6A, water molecules W1 and W2 are extracted in an interaction-calculation-target space including a target molecule P and one drug candidate molecule L1 in the second treatment. Meanwhile, a water molecule W1 is extracted in an interaction-calculation-target space including the target molecule P and another drug candidate molecule L2 in the second treatment, as illustrated in FIG. 6B. In this case, the water molecule W1 is present on the same coordinates in the two interaction-calculation-target spaces. On the other hand, the water molecule W2 is not present on the same coordinates in the two interaction-calculation-target spaces. Accordingly, the water molecule W2 is extracted in the non-overlapping water molecule extraction treatment.

Next, one example of the calculation-target water molecule extraction step is explained.

Figure 7:
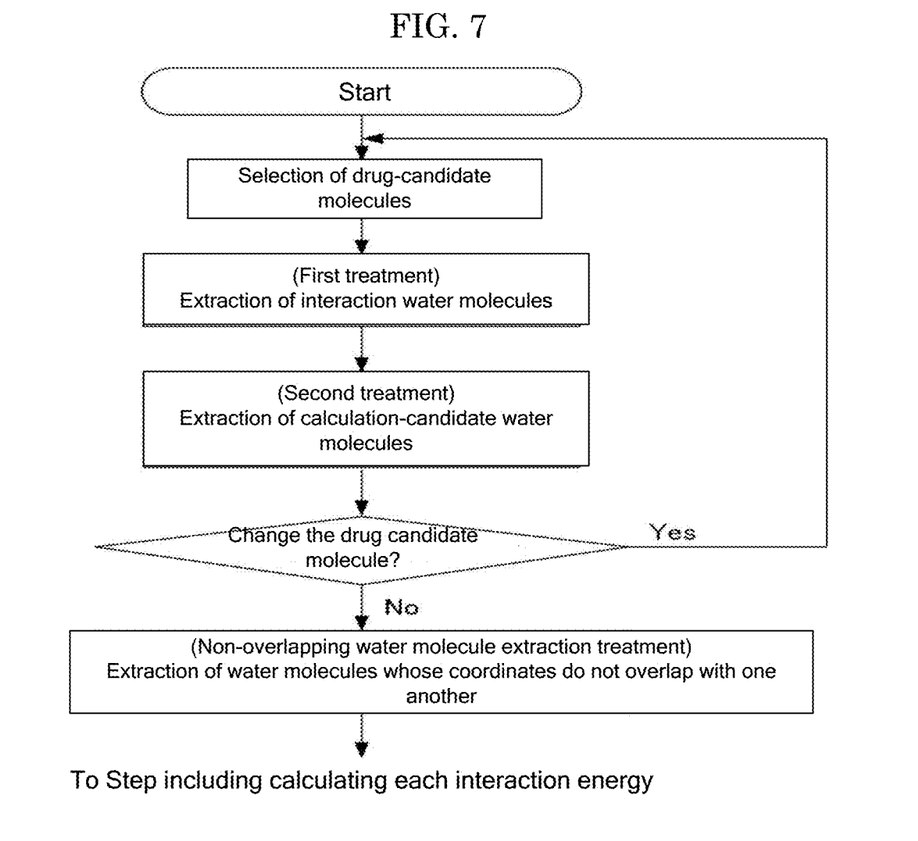
FIG. 7 is a flowchart of an example of a calculation-target water molecule extraction step.

FIG. 7 is a flowchart illustrating one example of the calculation-target water molecule extraction step.

First, one drug candidate molecule is selected.

Next, water molecules that interact with both a target molecule and the one drug candidate molecule are extracted (first treatment).

Next, water molecules are further extracted from the water molecules extracted in the first treatment based on a fluctuation width of coordinates of each of the water molecules, occurrence frequency of each of the water molecules, or both (second treatment).

Next, the drug candidate molecule is changed to perform the first treatment and the second treatment on another drug candidate molecule.

Next, the first treatment and the second treatment are performed on the above-mentioned another drug candidate molecule.

When the first treatment and the second treatment are completed on a plurality of drug candidate molecules with which interaction energy of the target molecule are to be determined, the process is moved onto a non-overlapping water molecule extraction treatment.

In the non-overlapping water molecule extraction treatment, a plurality of interaction-calculation-target spaces are compared, and one or more water molecules, which are not on the same coordinates in all of the complexes each including the target molecule and each drug candidate molecule, are extracted from the water molecules extracted in the second treatment.

Then, one example of the calculation-target water molecule extraction step is completed.

Interaction Energy Calculation Step

In the interaction energy calculation step, each interaction energy between the target molecule and each of the drug candidate molecules is calculated with only considering the one or more calculation-target water molecules as water molecules treated positively in a calculation of each interaction energy, and with considering the one or more calculation-target water molecules only in a calculation of interaction energy which the one or more calculation-target water molecules influence.

In the present specification, the phrase "treated positively" means to consider explicitly as a molecule. Examples of a method for not treating positively include a method where water molecules are treated negatively by continuum approximation.

The interaction energy calculation step preferably includes a below-mentioned treatment A, a below-mentioned treatment B, and a below-mentioned treatment C, when each interaction energy between the target molecule and the one drug candidate molecule among the drug candidate molecules is calculated, and preferably further includes a below-mentioned treatment D, when the one or more calculation-target water moleucles are considered at the time when each interaction energy between the target molecule and the one drug candidate molecule is calculated, because reliability of a relative relationship between calculated values of interaction energy is enhanced.

Note that, an order for performing the above-mentioned treatments is not limited.

Treatment A

In the treatment A, pair interaction energy between the target molecule and the one drug candidate molecule, which are in a complex of the target molecule and the one drug candidate molecule, is calculated.

Treatment B

In the treatment B, polarization interaction energy of the target molecule alone, which is the target molecule of the complex, is calculated.

The polarization interaction energy is polarized energy within the target molecule, which is generated when the target molecule forms a complex with the one drug candidate molecule from a state of the target molecule alone.

For example, the polarization interaction energy can be determined by the following method.

Energy ($E_{P0}$) of a state of the target molecule alone is calculated. At the time of the calculation, a virtual water molecule is arranged at the surroundings of the target molecule. For example, the arrangement of the virtual water molecule can be performed by continuum approximation.

Energy ($E_{P1}$) of the target molecule in the complex is calculated. At the time of the calculation, a virtual water molecule is arranged at the surroundings of the complex. For example, the arrangement of the virtual water molecule can be performed by continuum approximation.

Then, the polarization interaction energy is determined from a difference between the energy ($E_{P0}$) and the energy ($E_{P1}$).

Treatment C

In the treatment C, polarization interaction energy of the one drug candidate molecule alone, which is the one drug candidate molecule in the complex, is calculated.

The polarization interaction energy is polarized energy within the one drug candidate molecule and is generated when the drug candidate molecule forms the complex with the target molecule from the state of the one drug candidate molecule alone.

For example, the polarization interaction energy can be determined by the following method.

Energy ($E_{L0}$) of a state of the one drug candidate molecule alone is calculated. At the time of the calculation, a virtual water molecule is arranged in the surroundings of the one drug candidate molecule. For example, the arrangement of the virtual water molecule can be performed by continuum approximation.

Energy ($E_{L1}$) of the one drug candidate molecule in the complex is calculated. At the time of the calculation, a virtual water molecule is arranged in the surroundings of the complex. For example, the arrangement of the virtual water molecule can be performed by continuum approximation.

Then, the polarization interaction energy is determined from a difference between the energy ($E_{L0}$) and the energy ($E_{L1}$).

Treatment D

In the treatment D, pair interaction energy between the calculation-target water molecule and the one drug candidate molecule is calculated.

The treatment D is performed when the one or more calculation-target water moleucles are considered at the time when each interaction energy between the target molecule and the one drug candidate molecule is calculated.

In the case where the calculation-target water molecule is not present in one interaction-calculation-target space including the target molecule and the one drug candidate molecule, the treatment D is not performed at the time when the interaction energy between the target molecule and the one drug candidate molecule is calculated.

In the treatment D, the calculation-target water molecule is preferably regarded as part of the target molecule because accuracy of the interaction energy calculated improves.

In the case where the calculation-target water molecule is considered at the time when the interaction energy between the target molecule and the one drug candidate molecule is calculated, the calculation-target water molecule is preferably considered in the treatment A, the treatment B, and the treatment C because accuracy of the interaction energy calculated improves.

When the calculation-target water molecule is considered, the calculation-target water molecule is preferably regarded as part of the complex.

For example, the interaction energy calculation step can be performed by quantum mechanics (QM) calculations. Examples of the quantum mechanics calculations include molecule orbital calculations according to a molecular orbital method. Examples of the molecular orbital calculations include nonempirical molecular orbital calculations (ab initio molecular orbital calculation), and semiempirical molecular orbital calculations.

Examples of a methodology of the nonempirical molecular orbital calculation include the Hartree-Fock method, and the electron correlation method.

Examples of a methodology of the semiempirical molecular orbital calculation include CNDO, INDO, AM1, and PM3.

Examples of a program of the nonempirical molecular orbital calculation include Gaussian03, GAMESS, ABINIT-MP, and Protein DF.

Examples of a program of the semiempirical molecular orbital calculation include MOPAC.

Next, one example of a step where each of the interaction energy is calculated is explained.

Figure 8:
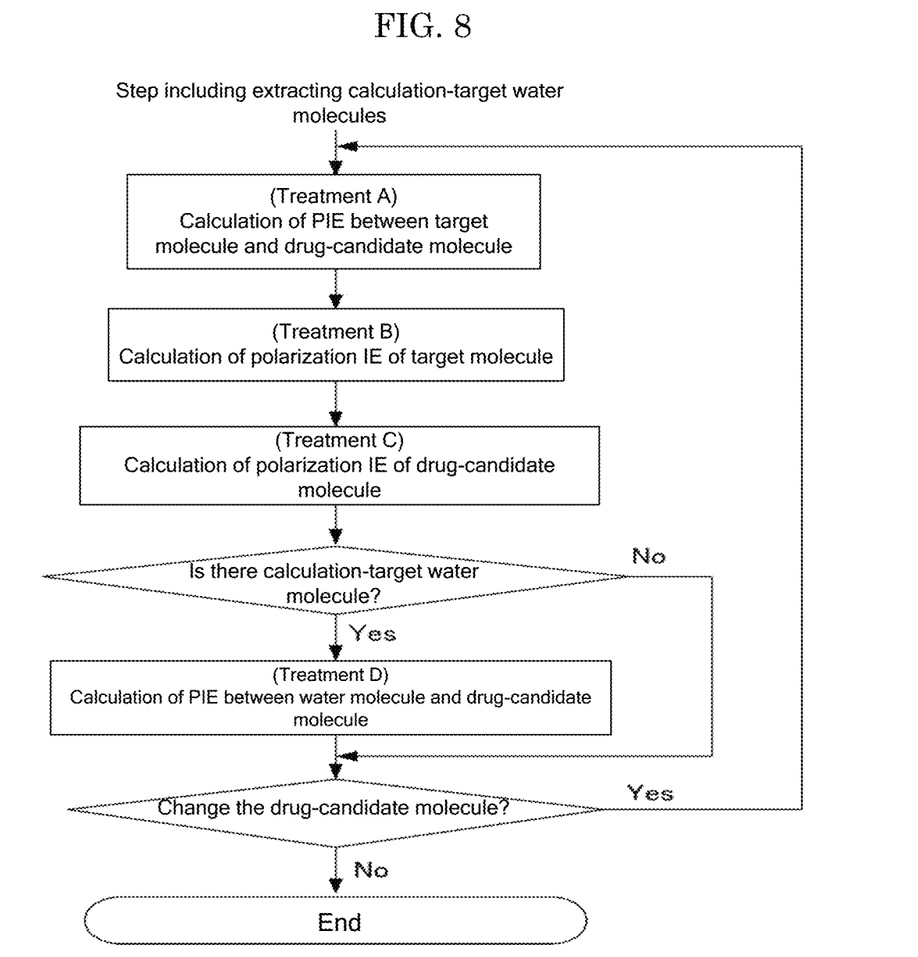
FIG. 8 is a flowchart of an interaction energy calculation step.

FIG. 8 is a flowchart of one example of a step where each of the interaction energy is calculated.

First, a pair interaction energy (PIE) between the target molecule and one drug candidate molecule in a complex of the target molecule and the one drug candidate molecule is calculated (treatment A).

Next, polarization interaction energy (polarization IE) of the target molecule is calculated (treatment B).

Next, polarization interaction energy (polarization IE) of the one drug candidate molecule is calculated (treatment C).

In the case where the calculation-target water molecule is present in one interaction-calculation-target space including the target molecule and the one drug candidate molecule, pair interaction energy (PIE) between the calculation-target water molecule and the one drug candidate molecule is calculated (treatment D). In the case where the calculation-target water molecule is not present in the one interaction-calculation-target space, on the other hand, the treatment D is not performed.

Next, the drug candidate molecule is changed in order to perform the treatment A, the treatment B, and the treatment C on another drug candidate molecule, as well as the treatment D in the case where the calculation-target water molecule is present in one interaction-calculation-target space including the target molecule and another drug candidate molecule.

Next, the treatment A, the treatment B, and the treatment C, as well as the treatment D in the case where the calculation-target water molecule is present in one interaction-calculation-target space including the target molecule and another drug candidate molecule, are performed on the above-mentioned another drug candidate molecule.

When the treatment A, the treatment B, the treatment C, and optionally the treatment D according to the above-described conditions are completed on all of the drug candidate molecules with which interaction energy of the target molecule is to be determined, the present step is completed.

For example, the method for calculating interaction energy can be performed by means of any of general computer systems (e.g., various network servers, work stations, and personal computers) including central processing units (CPUs), random access memories (RAMs), hard disks, can various computer peripherals.

Program

The disclosed program is a program for causing a computer to execute the disclosed method for calculating interaction energy.

A preferable embodiment for executing the method for calculating interaction energy is identical to a preferable embodiment of the method for calculating interaction energy.

The program can be created using any of various programing languages known in the art according to a configuration of a computer system for use, a type or version of an operation system for use.

The program may be recorded on a non-transitory recording medium, such as an integral hard disk, and an external hard disk, or recorded on a non-transitory recording medium, such as a compact disc read only memory (CD-ROM), a digital versatile disk read only memory (DVD-ROM), a magneto-optical (MO) disk, and a universal serial bus (USB) memory stick (USB flash drive). In the case where the program is recorded on a non-transitory recording medium, such as a CD-ROM, a DVD-ROM, an MO disk, and an USB memory stick, the program can be used, as required, directly or by installing a hard disk via a non-transitory recording medium reader equipped in a computer system. Moreover, the program may be recorded in an external memory region (e.g. another computer) accessible from the computer system via an information and communication network, and the program may be used, as required, by directly from the external memory region or installing into a hard disk from the external memory region via the information and communication network.

The program may be divided into predetermined processes and recorded on a plurality of non-transitory recording mediums.

Computer-Readable Non-Transitory Recording Medium

The disclosed computer-readable non-transitory recording medium includes the disclosed program stored thereon.

The computer-readable non-transitory recording medium is not particularly limited and may be appropriately selected depending on the intended purpose. Examples of the computer-readable non-transitory recording medium include integral hard disks, external hard disks, CD-ROMs, DVD-ROMs, MO disks, and USB memory sticks.

The non-transitory recording medium may be a plurality of non-transitory recording mediums to which the program is divided into the predetermined processes and recorded.

Interaction Energy Calculation Device

One embodiment of the disclosed interaction energy calculation device includes at least an extracting unit and a calculating unit, and may further include other units according to the necessity.

The extracting unit is configured to extract one or more calculation-target water molecules that influence at least interaction energy between a target molecule and some of drug candidate molecules, but not the interaction energy between the target molecule and all of the drug candidate molecules.

The calculating unit is configured to calculate each interaction energy between the target molecule and each of the drug candidate molecules with only considering the one or more calculation-target water molecules as water molecules treated positively in a calculation of each interaction energy, and with considering the one or more calculation-target water molecules only in a calculation of interaction energy which the one or more calculation-target water molecules influence.

Another embodiment of the disclosed interaction energy calculation device includes an extracting unit, and may further include other units according to the necessity.

In this embodiment, the extracting unit is configured to extract one or more calculation-target water molecules.

In this embodiment, the one or more calculation-target water molecules influence at least interaction energy between a target molecule and some of drug candidate molecules, but not the interaction energy between the target molecule and all of the drug candidate molecules.

In this embodiment, only the one or more calculation-target water molecules are considered as water molecules treated positively in a calculation of each interaction energy, and are only considered in a calculation of interaction energy which the one or more calculation-target water molecules influence.

In this embodiment, the one or more calculation-target water molecules are used for calculating interaction energy between the target molecule and the drug candidate molecules.

Yet another embodiment of the disclosed interaction energy calculation device includes a calculating unit, and may further include other units according to the necessity.

In this embodiment, the calculating unit is configured to calculate each interaction energy between a target molecule and each of drug candidate molecules with only considering extracted one or more calculation-target water molecules as water molecules treated positively in a calculation of each interaction energy, and with considering the one or more calculation-target water molecules only in a calculation of interaction energy which the one or more calculation-target water molecules influence, in which the one or more calculation-target water molecules influence at least interaction energy between the target molecule and some of the drug candidate molecules, but not the interaction energy between the target molecule and all of the drug candidate molecules.

A preferable embodiment of a processing method of each unit in the interaction energy calculation device is identical to the preferable embodiment of each step of the method for calculating interaction energy.

The calculation device may be a plurality of calculation devices including a plurality of non-transitory recording mediums in which the program is divided by the predetermined processes, and recorded.

Figure 9:
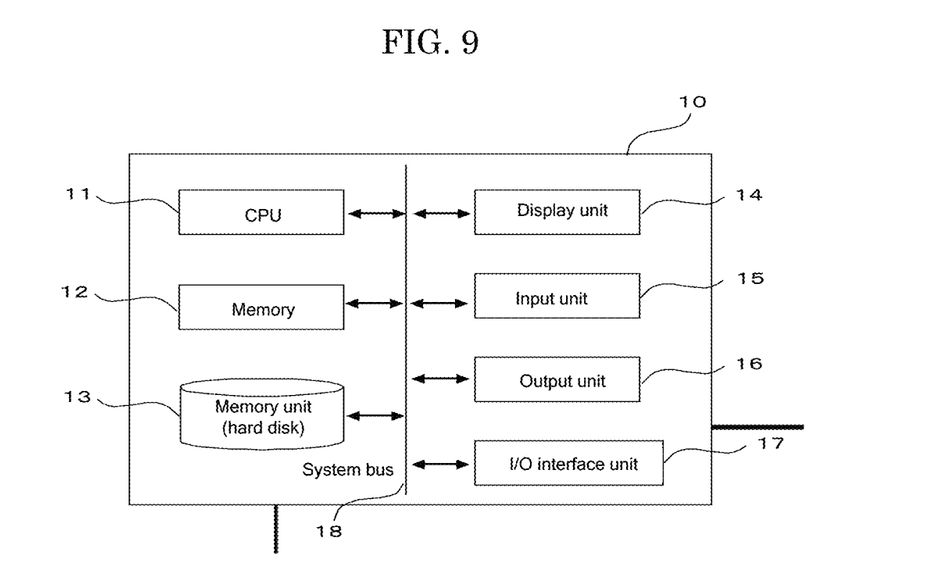
FIG. 9 is a view illustrating a structural example of the disclosed calculation device.

A structural example of the disclosed calculation device is illustrated in FIG. 9.

The calculation device 10 is composed by connecting CPU 11, a memory 12, a memory unit 13, a display unit 14, an input unit 15, an output unit 16, an I/O interface unit 17, ect. via a system bus 18.

The central processing unit (CPU) 11 is configured to perform calculation (e.g., four arithmetic operation, relational operation, etc.), and control of operations of hardware and software.

The memory 12 is a memory, such as a random access memory (RAM), and a read only memory (ROM). The RAM is configured to store an operation system (OS) and application programs read from the ROM and the memory unit 13, and function as a main memory and work area of the CPU 11.

The memory unit 13 is a device for storing various programs and data. For example, the memory unit 13 is a hard disk. In the memory unit 13, programs to be executed by the CPU 11, data required for executing the programs, and an OS are stored.

The program is stored in the memory unit 13, loaded on the RAM (a main memory) of the memory 12, and executed by the CPU 11.

The display unit 14 is a display device. For example, the display unit is a display device, such as a CRT monitor, and a liquid crystal panel.

The input unit 15 is an input device for various types of data. Examples of the input unit include a key board, and a pointing device (e.g., a mouse).

The output unit 16 is an output device for various types of data. For example, the output unit is a printer.

The I/O interface unit 17 is an interface for connecting to various external devices. For example, the I/O interface unit enables input and output of data of CD-ROMs, DVD-ROMs, MO disks, and USB memory sticks.

Figure 10:
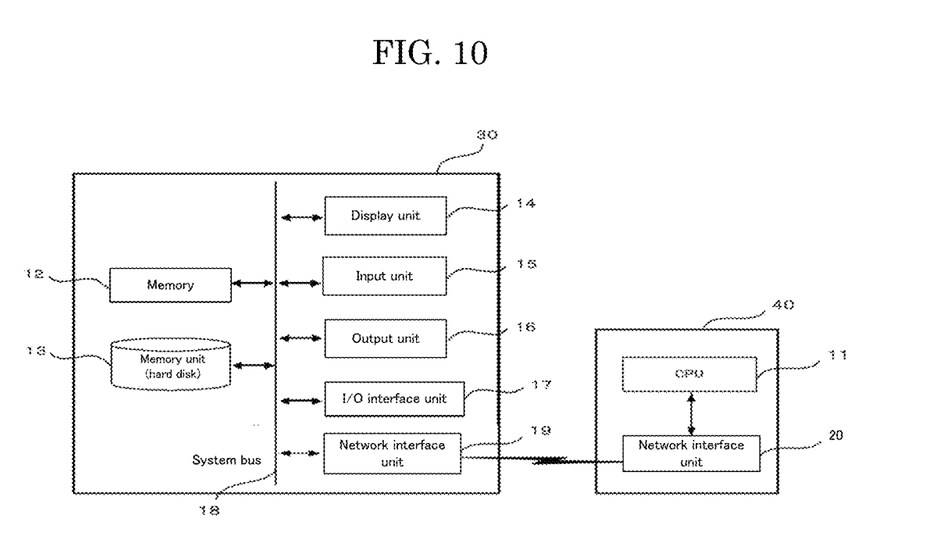
FIG. 10 is a view illustrating another structural example of the disclosed calculation device.

Another structural example of the disclosed calculation device is illustrated in FIG. 10.

The structural example of FIG. 10 is a structural example of a cloud-type calculation device, where a CPU 11 is independent from a memory unit 13. In the structural example, a computer 30 storing therein the memory unit 13 and a computer 40 storing therein the CPU 11 are coupled with each other through network interface units 19 and 20.

The network interface units 19 and 20 are hardware configured to communicate using the internet.

Figure 11:
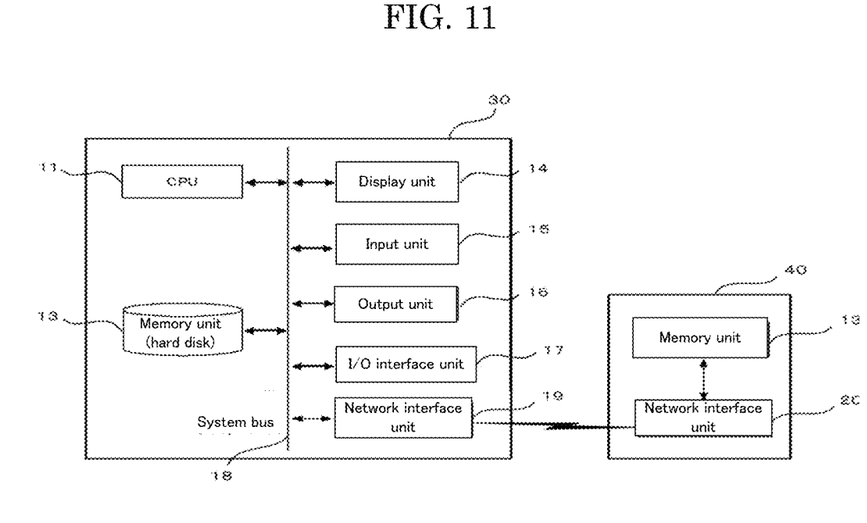
FIG. 11 is a view illustrating another structural example of the disclosed calculation device.

FIG. 11 illustrates another structural example of the disclosed calculation device.

The structural example of FIG. 11 is a structural example of a cloud-type calculation device, where a memory unit 13 is independent from CPU 11. In the structural example, a computer 30 storing therein the CPU 11 and a computer 40 storing therein the memory unit 13 are coupled with each other through network interface units 19 and 20.

An interaction energy calculation device according to an embodiment includes a calculating unit configured to calculate each interaction energy between a target molecule and each of drug candidate molecules with only considering extracted one or more calculation-target water molecules as water molecules treated positively in a calculation of each interaction energy, and with considering the one or more calculation-target water molecules only in a calculation of interaction energy which the one or more calculation-target water molecules influence, wherein the one or more calculation-target water molecules influence at least interaction energy between the target molecule and some of the drug candidate molecules, but not the interaction energy between the target molecule and all of the drug candidate molecules.

EXAMPLES

The disclosed technology is explained hereinafter, but Examples below shall not be construed as to limit the scope of the disclosed technology.

Example 1

The disclosed method for calculating interaction energy was performed according to the flows depicted in FIGS. 1, 7, and 8.

As a target molecule, a blood coagulation factor Xa, which was protein, was used.

As drug candidate molecules, four ligands (RRP, RTR, RDR, and RRR) were used.

It has been known that a complex structure of the blood coagulation factor Xa and each of four ligands (RRP, RTR, RDR, and RRR) is a PDB crystal structure (1NFU, 1NFY, 1NFX, and 1NFW, respectively).

When a fluctuation width of coordinates of each water molecule and occurrence frequency of the water molecule were determined, a molecular dynamic simulation using the PDB crystal structure as an initial value was performed for 10 ns.

Note that, in the first treatment, a threshold of a distance was set to 3 angstroms, and water molecules, distances of which from the target molecule and the drug candidate molecule were 3 angstroms or less, were extracted.

When extraction of water molecules based on a fluctuation width of coordinates of each water molecule was performed in the second treatment, moreover, a threshold of a value of RMSF was set to 2 angstroms, and water molecules having the RMSF value of 2 angstroms or less were extracted.

Moreover, occurrence frequency of the water molecule in the second treatment was determined from a density distribution of water molecules obtained by disposing all of water molecules for a period of 2 ns from the termination of the molecular dynamic simulation in one space. Then, coordinates having 10 times the density of an arbitral low density region in the density distribution of the water molecules was selected, and a virtual water molecule was determined to be present on the coordinates.

Water molecules were extracted according to the flow of FIG. 7. As a result, two water molecules present only adjacent to RRR could be extracted.

Next, interaction energy between the blood coagulation factor Xa and each of the four ligands (RRP, RTR, RDR, and RRR) was calculated according to the flow of FIG. 8. Only in the calculation of interaction energy between the blood coagulation factor Xa and the ligand RRR, the extracted two water molecules were considered.

Figure 12:
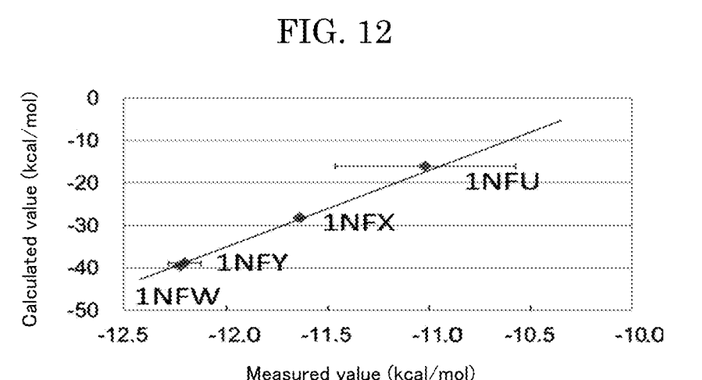
FIG. 12 is a graph presenting the result of Example 1.

The obtained four values of the interaction energy, and the measured values of the interaction energy between the blood coagulation factor Xa and the four ligands (RRP, RTR, RDR, and RRR) were compared. The results are presented in FIG. 12. The value on the horizontal axis is a measured value, and the value on the vertical axis is an interaction energy value (calculated value) calculated by the above-described method. A linear correlation was obtained between the measured value and the calculated value.

Comparative Example 1

Interaction energy between a blood coagulation factor Xa and each of four ligands (RRP, RTR, RDR, and RRR) was calculated in the same manner as in Example 1, except that extraction of water molecules was not performed.

Figure 13:
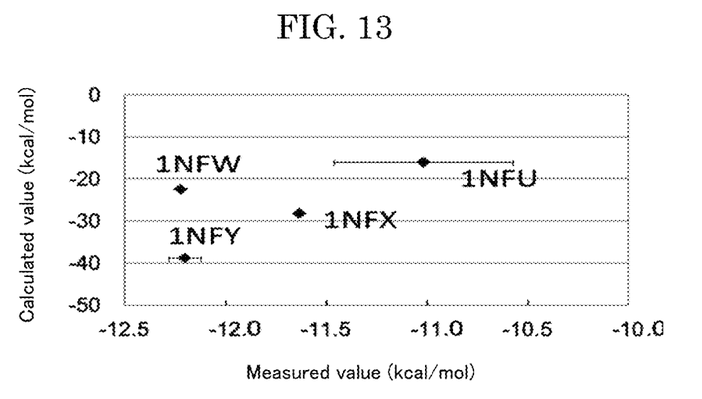
FIG. 13 is a graph presenting the result of Comparative Example 1.

The obtained four values of the interaction energy, and the measured values of the interaction energy between the blood coagulation factor Xa and the four ligands (RRP, RTR, RDR, and RRR) were compared. The results are presented in FIG. 13. The value on the horizontal axis is a measured value, and the value on the vertical axis is an interaction energy value (calculated value) calculated by the above-described method. A linear correlation was not obtained between the measured value and the calculated value.

Example 1 hardly increased the calculation time of the interaction energy compared to Comparative Example 1.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the sprit and scope of the invention.

What is claimed is:

1. A method for calculating interaction energy between a target molecule and drug candidate molecules, the method comprising:

determining one or more calculation-target water molecules that influence at least interaction energy between the target molecule and some of the drug candidate molecules, but not the interaction energy between the target molecule and all of the drug candidate molecules; and calculating each interaction energy between the target molecule and each of the drug candidate molecules with only considering the one or more calculation-target water molecules as water molecules treated positively in a calculation of each interaction energy, and with considering the one or more calculation-target water molecules only in a calculation of interaction energy which the one or more calculation-target water molecules influence, wherein the one or more calculation-target water molecules are one or more water molecules that influence at least interaction energy between the target molecule and some of the drug candidate molecules, but not the interaction energy between the target molecule and all of the drug candidate molecule, wherein the method is a method for calculating interaction energy between the target molecule and the drug candidate molecules using a computer.

2. The method according to claim 1, wherein the determining the one or more calculation-target water molecules includes a first treatment and a second treatment in one interaction-calculation-target space including the target molecule and one drug candidate molecule among the drug candidate molecules, where the first treatment includes determining one or more interaction water molecules that interact with both the target molecule and the one drug candidate molecule, and the second treatment includes determining one or more calculation-candidate water molecules from the one or more interaction water molecules based on a fluctuation width of coordinates of each of the one or more interaction water molecules, or occurrence frequency of each of the one or more interaction water molecules, or both, and wherein the determining the one or more calculation-target water molecules further includes a treatment including comparing at least interaction-calculation-target spaces each including the one or more calculation-candidate water molecules among all of the interaction-calculation-target spaces each including the target molecule and the drug candidate molecules, to determine one or more water molecules, which do not have identical coordinates in all of the interaction-calculation-target spaces, from the one or more calculation-candidate water molecules.

3. The method according to claim 2,
wherein the second treatment is a treatment including determining the one or more calculation-candidate water molecules among the one or more interaction water molecules based on a fluctuation width of coordinates of each of the one or more interaction water molecules, and occurrence frequency of each of the one or more interaction water molecules.

4. The method according to claim 2,
wherein the fluctuation width of the coordinates of each of the one or more interaction water molecules and the occurrence frequency of each of the one or more interaction water molecules are determined by molecular dynamic simulation.

5. An interaction energy calculation device, comprising:
one or more processors; and
a memory storing instructions that, when executed by the one or more processors, cause the interaction energy calculation device to:
determine one or more calculation-target water molecules that influence at least interaction energy between a target molecule and some of drug candidate molecules, but not the interaction energy between the target molecule and all of the drug candidate molecules; and
calculate each interaction energy between the target molecule and each of the drug candidate molecules with only considering the one or more calculation-target water molecules as water molecules treated positively in a calculation of each interaction energy, and with considering the one or more calculation-target water molecules only in a calculation of interaction energy which the one or more calculation-target water molecules influence,
wherein the one or more calculation-target water molecules are one or more water molecules that influence at least interaction energy between the target molecule and some of the drug candidate molecules, but not the interaction energy between the target molecule and all of the drug candidate molecule.

6. The interaction energy calculation device according to claim 5,
wherein instructions that, when executed by the one or more processors, further cause the interaction energy calculation device to execute a first treatment and a second treatment in one interaction-calculation-target space including the target molecule and one drug candidate molecule among the drug candidate molecules,
where the first treatment includes determining one or more interaction water molecules that interact with both the target molecule and the one drug candidate molecule, and
the second treatment includes determining one or more calculation-candidate water molecules from the one or more interaction water molecules based on a fluctuation width of coordinates of each of the one or more interaction water molecules, or occurrence frequency of each of the one or more interaction water molecules, or both, and
wherein the instructions that, when executed by the one or more processors, further cause the interaction energy calculation device to further execute a treatment including comparing at least interaction-calculation-target spaces each including the one or more calculation-candidate water molecules among all of the interaction-calculation-target spaces each including the target molecule and the drug candidate molecules, to determine one or more water molecules, which do not have identical coordinates in all of the interaction-calculation-target spaces, from the one or more calculation-candidate water molecules.

7. The interaction energy calculation device according to claim 6,
wherein the second treatment is a treatment including determining the one or more calculation-candidate water molecules among the one or more interaction water molecules based on a fluctuation width of coordinates of each of the one or more interaction water molecules, and occurrence frequency of each of the one or more interaction water molecules.

8. The interaction energy calculation device according to claim 6,
wherein the fluctuation width of the coordinates of each of the one or more interaction water molecules and the occurrence frequency of each of the one or more interaction water molecules are determined by molecular dynamic simulation.

9. An interaction energy calculation device comprising:
one or more processors; and
a memory storing instructions that, when executed by the one or more processors, cause the interaction energy calculation device to:
determine one or more calculation-target water molecules,
wherein the one or more calculation-target water molecules influence at least interaction energy between a target molecule and some of drug candidate molecules, but not the interaction energy between the target molecule and all of the drug candidate molecules,
the one or more calculation-target water molecules are one or more water molecules that influence at least interaction energy between the target molecule and some of the drug candidate molecules, but not the interaction energy between the target molecule and all of the drug candidate molecule,
only the one or more calculation-target water molecules are considered as water molecules treated positively in a calculation of each interaction energy, and are only considered in a calculation of interaction energy which the one or more calculation-target water molecules influence, and
the one or more calculation-target water molecules are used for calculating interaction energy between the target molecule and the drug candidate molecules.

* * * * *